United States Patent [19]

Nalepa et al.

[11] Patent Number: 5,008,453

[45] Date of Patent: Apr. 16, 1991

[54] AROMATIC DIIMINES

[75] Inventors: Christopher J. Nalepa; J. Kenneth Presswood; Gordon G. Knapp, all of Baton Rouge, La.

[73] Assignee: Ethyl Corporation, Richmond, Va.

[21] Appl. No.: 338,986

[22] Filed: Apr. 14, 1989

[51] Int. Cl.$^5$ ............................................ C07C 251/16
[52] U.S. Cl. ..................................... 564/271; 528/59; 564/277
[58] Field of Search ................................. 564/271, 277

[56] References Cited

U.S. PATENT DOCUMENTS

| | | | |
|---|---|---|---|
| 2,000,039 | 5/1935 | Semon et al. | 564/271 |
| 2,300,678 | 11/1942 | Kharasch et al. | 564/271 |
| 2,929,797 | 3/1960 | Albert | 564/271 |
| 2,965,605 | 12/1960 | Reynolds et al. | 564/271 |
| 3,135,796 | 6/1964 | Layer et al. | 564/271 |
| 3,207,813 | 9/1965 | Harvey | 564/271 |

FOREIGN PATENT DOCUMENTS 63-130571  6/1988  Japan ................................ 564/271

*Primary Examiner*—James H. Reamer
*Attorney, Agent, or Firm*—Richard J. Hammond; Patricia J. Hogan

[57] ABSTRACT

Aromatic diimines having one or two benzene rings, two ar-imino substituents corresponding to the formula —N=CH$_2$, and ar-alkyl substituents in all positions ortho to the imino substituents are novel compounds which can be used in the preparation of polyurethanes, polyureas, polyurethane-urea polymers, and epoxy resins.

8 Claims, No Drawings

AROMATIC DIIMINES

FIELD OF INVENTION

This invention relates to aromatic diimines and more particularly to sterically hindered aromatic diimines which can be used in the preparation of polyurethane, polyurea, polyurethane-urea, and epoxy resins.

BACKGROUND

There are many polyfunctional compounds, including diols and aromatic diamines, which are known to be useful as chain extenders in the preparation of polyurethane, polyurea, and polyurethane-urea polymers and/or as curing agents for epoxy resins. None of these compounds has a reactivity such as to make it universally ideal, and many fail to provide satisfactory properties in the products made by their use. Thus, there is still a need to find other compounds capable of serving as chain extenders of curing agents.

U. S. Pat. No. 4,794,129 (Gillis et al.) teaches the use of certain imino-functional compounds as chain extenders in preparing polyureas by RIM processes, and the speculative teachings of the patent include the use as chain extenders of aromatic imines wherein the aromatic group is attached to the carbon of the imino unit.

SUMMARY OF INVENTION

An object of this invention is to provide novel sterically hindered aromatic diimines.

Another object is to provide polyurethane, polyurea, polyurethane-urea, and epoxy resins prepared from such aromatic diimines.

These and other objects are attained by (A) providing an aromatic diimine having one or two benzene rings, two ar-imino substituents corresponding to the formula —N=CH$_2$, and ar-alkyl substituents in all positions ortho to the imino substituents and (B) when desired, using the aromatic diimine to prepare a polyurethane, polyurea, polyurethane-urea, or epoxy resin.

DETAILED DESCRIPTION

The aromatic diimines of the invention may be any of the aromatic diimines described in the preceding paragraph, including such diimines wherein the alkyl groups have rather long carbon chains, e.g., chains of up to about 20 carbons. However, it is generally preferred that the compounds be aromatic diimines in which the ar-alkyl substituents are straight- or branched-chain alkyl groups of 1-6 carbons, e.g., methyl, ethyl, propyl, isopropyl, butyl, t-butyl, pentyl- hexyl, etc. These alkyl substituents may be the same or different.

In a preferred embodiment of the invention, the aromatic diimine is a compound corresponding to the formula:

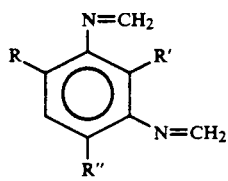

wherein R, R', and R" are independently selected from alkyl groups containing 1-6 carbons; and it is most preferably such a compound in which at least two of the alkyl substituents contain at least two carbons. Of these compounds, those particularly preferred are the aromatic diimine in which R is methyl and R' and R" are ethyl, the aromatic diimine in which R' is methyl and R and R" are ethyl, and mixtures thereof. In another preferred embodiment of the invention, the aromatic diimine is a compound corresponding to the formula:

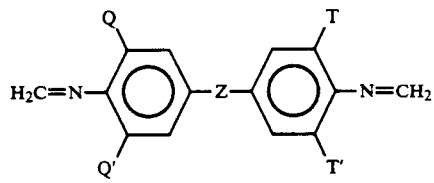

wherein Q, Q', T, and T' are independently selected from alkyl groups containing 1-6 carbons and Z is an alkylidene group containing 1-3 carbons. A particularly preferred aromatic diimine of this type is the compound wherein Q, Q', T, and T' are ethyl and Z is methylene.

Regardless of the particular type of compound involved, the aromatic diimines of the invention are prepared by reacting formaldehyde with the aromatic diamine corresponding to the desired aromatic diimine, i.e., an aromatic diamine having one or two benzene rings, two primary amino groups attached to the ring or rings, and ar-alkyl substituents in all positions ortho to the amino substituents. Such compounds are well known and include, e.g., 3,5-diethyl-2,4-diaminotoluene, 3,5-diethyl-2,6-diaminotoluene, DETDA (a mixture of 3,5-diethyl-2,4-diaminotoluene and 3,5-diethyl-2,6-diaminotoluene), 1,3,5-triethyl-2,6-diaminobenzene, 3,5-diisopropyl-2,4-diaminotoluene, 3,5-di-sec-butyl-2,6-diaminotoluene, 3-ethyl-5-isopropyl-2,4-diaminotoluene, 3,3', 5,5'tetraethyl-4,4'-diaminodiphenylmethane (MBDEA), 3,3', 5,5'-tetraisopropyl-4,4'-diaminodiphenylmethane, 3,3'-dimethyl-5,5', -dit-butyl-4,4'-diaminodiphenylmethane.

Except for its use of such aromatic diamines, the formaldehyde/amine reaction is conducted by techniques known for converting amines to imines, e.g., the techniques disclosed in March, *Advanced Organic Chemistry*, Second Edition, McGraw-Hill (New York), page 817 (1977), and the references disclosed therein. It is generally preferred to employ 2-4 mols of formaldehyde per mol of aromatic diamine, to incorporate the formaldehyde in the form of paraformaldehyde, and to reflux a mixture of the reactants in toluene or other solvent which azeotropes with water in order to form the diimine, the water of reaction being removed during the course of the reaction. Then, after completion of the reaction, the diimine is isolated by conventional means.

Actually, it is somewhat surprising both that the diimines of the invention can be prepared by this process and that they are stable and isolable. The literature indicates t formaldehyde is analogous to higher aldehydes and to ketones in the iminization of amines, but it has not been found possible to obtain imines from the aromatic diamines used to prepare the present diimines when attempts have been made to react those diamines with acetaldehyde or acetone in the presence or absence of catalysts. Also, even though March indicates that the presence of an aryl group on the nitrogen or carbon of the imine group makes an imine stable, more recent literature (e.g., Distefano et al., *J. Chem. Soc. Perkin Trans. II*, 1985, pp. 623-1627) indicates that at least some of the compounds previously believed to be stable aromatic imines had been misidentified and were really polymers formed from unstable imines.

When the sterically hindered aromatic diimines are to be used as chain extenders in the preparation of polyurethane, polyurea, or polyurethane-urea polymers, they are simply substituted for the chain extenders that have previously been used in such processes or used in conjunction with the known chain extenders, e.g., aromatic diamines such as those mentioned above; the aromatic polyamines of U. S. Pat. Nos. 3,428,610 (Klebert), 4,218,543 (Weber et al.), 4,595,742 (Nalepa et al.), and 4,631,298 (Presswood), the teachings of all of which are incorporated herein in toto by reference; polyhydroxyalkanes containing 2-6 carbons and 2-3 hydroxyl groups, such as ethylene glycol, the 1,2- and 1,3-propylene glycols, the 1,4-, 1,2-, and 2,3-butanediols, 1,5-pentanediol, neopentyl glycol, 1,6-hexanediol, glycerol, 1,2,4-butanetriol, 1,2,6-hexanetriol; and mixtures thereof. Thus, the chain extender or mixture of chain extenders is reacted with an organic polyisocyanate and an active hydrogen-containing organic compound or with a prepolymer thereof having a free —NCO content of at least 0.1% by weight to form the desired polymer. Exemplary of the isocyanates and active hydrogen-containing organic compounds that can be used are those taught in Nalepa et al.

When the sterically hindered aromatic diimines are to be used as curing agents for epoxy resins, they are just substituted for the curing agents that have previously been used to cure such resins or used in conjunction with the known curing agents, e.g., the aromatic polyamines and/or polyhydroxyalkanes described above as known chain extenders. The epoxy resin may be any epoxy resin, i.e., it may be saturated or unsaturated, aliphatic, cycloaliphatic, aromatic, or heterocyclic. Exemplary of such resins are those taught in Lee et al., *Handbook of Epoxy Resins,* McGrawHill (New York), 1967, the teachings of which are incorporated herein in toto by reference.

The following examples are given to illustrate the invention and are not intended as a limitation thereof.

EXAMPLE I

Preparation of DETDA Diimine

A suitable reaction vessel was charged with 120.6g (0.678 mol) of DETDA, 58.0g (1.93 mol) of paraformaldehyde, 400 mL of toluene, and about 0.2g of sodium hydroxide pellet. The mixture was refluxed with azeotropic removal of water for two hours, at which time no more water was collected. Removal of the toluene at reduced pressure afforded 125.5g (91.7% yield) of an orange oil, which was filtered through glass wool into a bottle, placed under nitrogen, and determined by vpc to contain 1.7 area % DETDA, 2.0 area % DETDA monoimine (i.e., a product in which half of the amino groups of DETDA have been converted to —N=CH$_2$ groups), and 96.3 area % DETDA diimine, a mixture of compounds corresponding to the formulas:

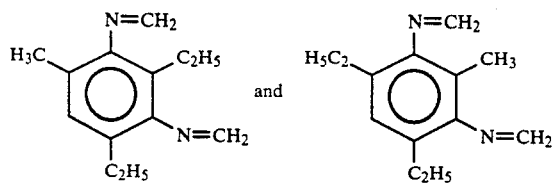

EXAMPLE II

Preparation of MBDEA Diimine

A suitable reaction vessel was charged with 105.1g (0.339 mol) of MBDEA, 31.5g (1.05 mol) of paraformaldehyde, 300 mL of toluene, and about 0.2g of sodium hydroxide pellet. The mixture was refluxed with azeotropic removal of water for 2.2 hours, at which time no more water was collected. Removal of the toluene at reduced pressure afforded 110.3g (96.0% yield) of an orange oil, which was filtered hot through a fritted glass Buchner funnel and determined by vpc to contain 2.0 area % MBDEA and 98.0 area % MBDEA diimine, a compound corresponding to the formula:

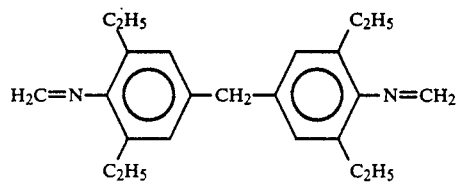

EXAMPLE III

Reactivity Determinations

Part A

With the equivalent weight of DETDA diimine assumed to be 101, a preheated stoichiometric portion of the DETDA diimine of Example I was mixed with 50g of a commercial toluenediisocyanate/polytetramethylene glycol ether prepolymer having a nominal free —NCO content of 4.2% preheated to 80° C. in a polypropylene cup. The reactivity was then determined by measuring the pour time (the expiration of the time after mixing when the reaction mixture could be poured out of the cup), gel time (the expiration of the time after mixing when the reaction mixture could flow under its own weight when the cup was rotated), tack time (the expiration of the time after mixing when the surface of the reaction mixture would stick to an object), and firm time (the amount of time after mixing until the reaction mixture would offer substantial resistance to manual pressure). The pour time was 34 minutes, the gel time 61 minutes, the tack time 67 minutes, and the firm time about 140 minutes.

Part B

A series of reaction mixtures was obtained by repeating Part A except for employing a commercial diphenylmethanediisocyanate/polytetramethylene ether glycol prepolymer having a nominal free —NCO content of 6.4% as the prepolymer, changing the temperature to 90° C., and employing the chain extenders indicated in Table I, which also shows the reactivity data in minutes (') and seconds ("). In this table, as well as elsewhere in the specification, DI represents DETDA diimine, BD represents 1,4-butanediol, E-300 represents a mixture of 3,5-di(methylthio)-2,4-diaminotoluene and 3,5-di(methylthio)-2,6-diaminotoluene, and the ratios shown are mol ratios.

TABLE I

| Chain Extender | Pour Time | Gel Time | Tack Time | Firm Time |
|---|---|---|---|---|
| DI | 2'05" | 3'15" | 4'10" | 6'30" |
| DI/BD (50/50) | 1'05" | 2'00" | 3'00" | 5'00" |
| DI/BD (25/75) | 1'15" | 2'45" | 4'00" | 6'00" |

TABLE I-continued

| Chain Extender | Pour Time | Gel Time | Tack Time | Firm Time |
|---|---|---|---|---|
| DI/BD (5/95) | 4'05" | 6'15" | 7'30" | 10'30" |
| DI/BD (1/99) | 5'30" | 8'20" | 9'00" | 17'00" |
| BD | 6'40" | 11'00" | 12'00" | 22'00" |
| E-300 | 25" | 39" | 39" | 53" |
| E-300/DI (50/50) | 45" | 1'10" | 1'10" | 3'00" |

As demonstrated in the preceding example, the diimines of the invention have reactivities such as to make them useful alone or in combination with other chain extenders in the preparation of polyurethane, polyurea, and polyurethane-urea polymers. It is also notable that the diimines can serve as catalysts for a diol/—NCO reaction and, at some concentrations, can provide reactivities greater than the reactivities of either the diol or the diimine alone.

The following example demonstrates that the use of the diimines permits the formation of polyurethanes having desirably low compression set and high resilience and hardness.

EXAMPLE IV

Physical Property Determinations

A series of polyurethanes was prepared by mixing chain extenders with the prepolymer of Example III, Part B, degassing the mixtures at 90° C., pouring them into molds in which they were heated at 100° C. for one hour, and post-curing them overnight at 100° C. Table II shows the stoichiometry (i.e., the percentage of the stoichiometric amount of chain extender) employed, as well as the physical properties determined by the usual ASTM procedures.

TABLE II

| Chain Extender | DI | DI | DI/BD (5/95) | BD |
|---|---|---|---|---|
| Stoichiometry, % | 92.5 | 99.6 | 95.0 | 94.0 |
| Hardness, A | 95 | 97 | 84 | 87 |
| Hardness, D | 47 | 47 | 36 | 36 |
| Tensile Strength, MPa | 16.1 | 16.6 | 16.6 | 32.1 |
| Elongation, % | 60 | 60 | 340 | 430 |
| Die C Tear, kg/m | 2143 | 1786 | 2679 | 5000 |
| D-470 Tear, kg/m | 54 | 36 | 482 | 1000 |
| Compression Set, % | 12 | 15 | 15 | 15 |
| Resilience, % | 60 | 59 | 61 | 65 |

In addition to comparing favorably with known diol and aromatic diamine chain extenders in the provision of acceptable physical properties at room temperature, the aromatic diimines of the invention have other advantages. For example, while a polyurethane prepared from the prepolymer of Example III, Part B, and 1,4-butanediol and having a Shore A hardness of 84 at 25° C. completely loses its hardness and melts at 175° C., a polyurethane prepared from the same prepolymer and DETDA diimine and having a Shore A hardness of 95 at 25° C. still retains about 95% of its hardness at 175° C. and still has a hardness of about 84 at 200° C. Also, as shown in the following example, the diimines of the invention provide polyurethanes having better solvent resistance because of their increased polymer crosslinking.

EXAMPLE V

Solvent Resistance Determinations

A series of polyurethanes was prepared from the prepolymer of Example III, Part B, and different chain extenders, formed into test specimens, and placed in tetrahydrofuran for 24 hours to determine the resistance of the polymers to solvent absorption. The chain extenders and stoichiometry employed in preparing the polyurethanes and the solvent swell data are shown in Table III.

TABLE III

| Chain Extender | Stoichiometry, % | Wt. Gain, % |
|---|---|---|
| BD | 95 | 515 |
| DI/BD (5/95) | 96 | 365 |
| DI | 92 | 83 |
| MBDEA diimine | 97 | 84 |
| MBDEA diimine | 88 | 78 |

The following example shows that the diimines of the invention can be used to prepare epoxy resins having acceptable glass transition temperatures and onset exothermic temperatures high enough to make them particularly useful for preparing prepregs.

EXAMPLE VI

Epoxy Resin Studies

The reactivities of DI and MBDEA diimine (MD) were evaluated by mixing each of them with a commercial diglycidyl ether of bisphenol A having an epoxide equivalent of 183, placing a drop of the sample to be tested in a Tg pan, scanning with a DSC at a heating rate of 10° C./min from 30° C. to 260-310° C., and determining the onset and peak exothermic temperatures as well as the glass transition temperatures. The results are shown in Table IV, which also shows the number of equivalents of curing agent employed and the maximum curing temperature (MCT) of the cure cycle used.

TABLE IV

| Curing Agent | Eq. | MCT (°C.) | Tg (°C.) | Onset (°C.) | Peak (°C.) |
|---|---|---|---|---|---|
| DI | 0.85 | 260 | — | 196 | 223 |
| DI | 1.0 | 260 | 69 | 205 | 219 |
| DI | 1.5 | 260 | 103 | 203 | 213 |
| DI | 2.0 | 260 | 96 | 204 | 212 |
| MD | 1.0 | 300 | 97 | 192 | 236 |
| DI | 0.85 | 300 | 63 | 195 | 222 |
| DI | 1.0 | 300 | 100 | 205 | 219 |
| DI | 1.0 | 310 | 112 | 204 | 220 |
| DI | 1.5 | 310 | 97 | 280 | 297 |
| DI | 2.0 | 310 | 77 | 266 | 286 |

It is obvious that many variations may be made in the products and processes set forth above without departing from the spirit and scope of this invention.

What is claimed is:

1. An aromatic diimine having one or two benzene rings and two ar-imino substituents corresponding to the formula

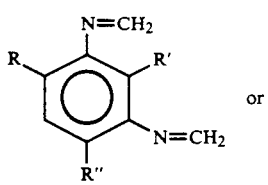

or

-continued

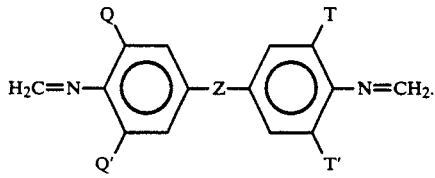

wherein R, R', and R" are independently selected from alkyl groups containing 1-6 carbons, Q, Q', T, and T' are independently selected from alkyl groups containing 1-6 carbons and Z is an alkylidene group containing 1-3 carbons.

2. An aromatic diimine of claim 1 corresponding to the formula:

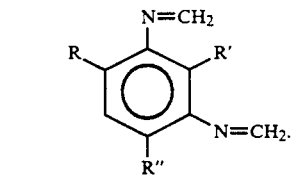

3. An aromatic diimine of claim 2 wherein at least two of the alkyl substituents contain at least two carbons.

4. An aromatic diimine of claim 3 wherein R is methyl and R' and R" are ethyl.

5. An aromatic diimine of claim 3 wherein R' is methyl and R and R" are ethyl.

6. A mixture of an aromatic diimine of claim 3 wherein R is methyl and R' and R" are ethyl and an aromatic diimine of claim 3 wherein R' is methyl and R and R" are thyl.

7. An aromatic diimine of claim 1 corresponding to the formula:

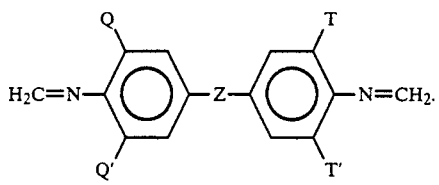

8. An aromatic diimine of claim 7 wherein Q, Q', T, and T' are ethyl and Z is methylene.

* * * * *